United States Patent [19]

Costantini et al.

[11] 4,026,947

[45] May 31, 1977

[54] PROCESS FOR THE OXIDATION OF β-ISOPHORONE

[75] Inventors: Michel Costantini; Adrien Dromard, both of Lyon; Michel Jouffret, Francheville, all of France

[73] Assignee: Rhone-Poulenc Industries, Paris, France

[22] Filed: Feb. 23, 1976

[21] Appl. No.: 660,721

[30] Foreign Application Priority Data

Nov. 3, 1975 France .............................. 75.07557

[52] U.S. Cl. ........................ 260/586 P; 260/593 R
[51] Int. Cl.$^2$ ...................................... C07C 45/00
[58] Field of Search ........ 260/586 P, 593 R, 597 R

[56] References Cited

UNITED STATES PATENTS

| 2,992,272 | 7/1961 | Hay | 260/586 P |
| 3,232,957 | 2/1966 | Sharp | 260/586 P |
| 3,354,220 | 11/1967 | Brackmann et al. | 260/586 P |
| 3,920,756 | 11/1975 | Tahara et al. | 260/586 P |
| 3,923,898 | 12/1975 | Schulte-Elte | 260/586 P |
| 3,931,327 | 1/1976 | Strickler et al. | 260/586 P |
| 3,944,620 | 3/1976 | Becker et al. | 260/586 P |
| 3,960,966 | 6/1976 | Widmer et al. | 260/586 P |

FOREIGN PATENTS OR APPLICATIONS 2,267,300  11/1975  France .......................... 260/586 P

OTHER PUBLICATIONS

Bailes, et al., "J.A.C.S.," 69, 1886–1893, (1947).

*Primary Examiner*—Norman Morgenstern

[57] ABSTRACT

A process for the oxidation of β-ethylenically unsaturated ketones, especially β-isophorone, is provided whereby the ketone is oxidized with a source of molecular oxygen in an organic liquid solvent in the presence of a base and certain chelate catalysts of cobalt or manganese as defined.

16 Claims, No Drawings

PROCESS FOR THE OXIDATION OF β-ISOPHORONE

BACKGROUND OF THE INVENTION

The present invention relates to a process for the oxidation of β-ethylenically-unsaturated ketone compounds and especially β-isophorone (3,5,5-trimethyl-cyclohex-3-en-1-one).

It is known that it is possible, using molecular oxygen, to oxidize α- or β-ethylenically-unsaturated carbonyl compounds carrying at least one hydrogen atom on the α- or γ- carbon atom, in the presence of a copper compound, a nitrogen-containing heterocyclic compound, a lower alkylamine and a lower alkanol (see U.S. Pat. No. 3,354,220). Depending on the reactant treated, dicarbonyl or hydroxycarbonyl ethylenically unsaturated compounds are obtained, together with by-products.

It has been found that the oxidation of β-ethylenically unsaturated ketone compounds to ethylenically-unsaturated dicarbonyl compounds, can be carried out in a more advantageous manner in the presence of certain catalysts.

It is an object of the present invention to provide an improved process for the oxidation of β-ethylenically unsaturated ketone compounds.

It is also an object of the present invention to provide an improved process for the continuous oxidation of β-ethylenically-unsaturated ketone compounds.

Other objects will be apparent to those skilled in the art from the present description.

GENERAL DESCRIPTION OF THE INVENTION

The present invention provides a process for the preparation of an ethylenically unsaturated dicarbonyl compound by oxidation of a β-ethylenically unsaturated ketone containing at least 5 carbon atoms and carrying at least one hydrogen atom on the α- and γ-carbon atom, which comprises oxidizing the ketone with molecular oxygen or a gas containing molecular oxygen, in a liquid organic solvent medium in the presence of an inorganic or organic base and a chelate of the general formula:

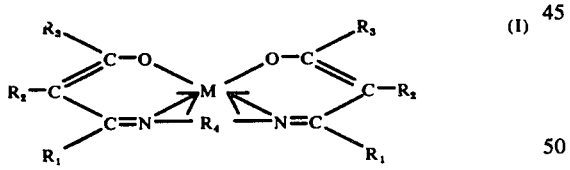

in which:

M represents cobalt or manganese, $R_1$, $R_2$ and $R_3$, which may be identical or different, each represents a hydrogen atom or an alkyl radical containing 1 to 4 carbon atoms; or $R_2$ and $R_3$, together with the 2 carbon atoms of the double bond, form a benzene ring carrying one or more hydrogen or halogen atoms, nitro groups, alkyl radicals containing 1 to 4 carbon atoms or alkoxy radicals containing 1 to 4 carbon atoms, and $R_4$ represents a divalent hydrocarbon radical containing 2 to 15 carbon atoms or an alkyl chain interrupted by one or more heteroatoms such as oxygen or nitrogen and containing from 4 to 10 carbon atoms.

The β-ethylenically-unsaturated ketone used in the process of the invention can be a straight-chain or branched-chain aliphatic compound containing 5 to 30 carbon atoms, or an alicyclic compound which has 5 to 16 carbon atoms in the ring and which is optionally substituted by alkyl radicals containing 1 to 4 carbon atoms such as methyl, ethyl and isobutyl radicals.

Aliphatic ketones which can be used include pent-4-en-2-one, 4-methyl-pent-4-en-2-one, hex-5-en-3-one, 3,4-dimethylhex-4-en-2-one, 4-methyl-3-ethyl-hex-4-en-2-one, hept-1-en-4-one, 6-methyl-hept-4-en-2-one and 2-methyl-hept-5-en-3-one.

Alicyclic ketones which can be used include cyclopent-3-en-1-one, cyclohex-3-en-1-one, 5,5-dimethyl-cyclohex-3-en-1-one, 2,5,5-trimethyl-cyclohex-3-en-1-one, 3,5,5-trimethyl-cyclohex-3-en-1-one (β-isophorone), 2,5,6-trimethyl-cyclohex-3-en-1-one, 2,6,6-trimethyl-cyclohex-3-en-1-one, 2,5,6,6-tetramethyl-cyclohex-3-en-1-one, 5,5-dimethyl-2-ethyl-cyclohex-3-en-1-one, 2-methyl-5-isopropyl-cyclohex,3-en-1-one, 5,5-dimethyl-2-isopropyl-cyclohex-3-en-1-one and cyclooct-3-en-1-one.

More desirably, the chelates used are those of general formula (I) in which $R_1$, $R_2$ and $R_3$ represent methyl, ethyl, propyl, isopropyl, butyl or isobutyl radicals; $R_4$ represents an alkylene (ethylene, propylene or butylene) radical, a cycloalkylene (cyclohexylene) radical, an arylene (o- or m-phenylene) radical or a 3-aza-(or oxa-)pentamethylene, 4-aza-(or oxa-) heptamethylene or 5-aza-(or oxa-)nonamethylene radical which may optionally be branched.

The chelates used preferentially are those of the general formula (I) in which $R_2$ and $R_3$, together with the 2 carbon atoms of the double bond, form a benzene ring optionally substituted by a nitro group.

Specific examples of chelates of the general formula (I), which are suitable for use in the present invention include condensation products of:

diamines such as ethylenediamine, propylene-1,2-diamine, propylene-1,3-diamine, butylene-1,4-diamine and o-phenylene-diamine, or of diamino-dialkylamines such as β, β'-diamino-diethylamine, γ,γ'-diamino-di-(n-propyl)amine, δ,δ'-diamino-di-(n-butyl) amine and N,N-di-(γ-amino-n-propyl)-methyl-amine, and of β-dicarbonyl or hydroxycarbonyl compounds such as β-di-ketones like pentane-2,4-dione, 3-methyl-pentane-2,4-dione, 3-ethyl-pentane-2,4-dione, hexane-2,4-dione, 3-methyl-hexane-2,4-dione, heptane-2,4-dione, heptane-3,5-dione, 4-methyl-heptane-3,5-dione, octane-2,4-dione and octane-3,5-dione; β-ketoaldehydes like propionylacetaldehyde; and hydroxycarbonyl compounds like 2-hydroxy-acetophenone, 2-hydroxy-benzaldehyde, 2-hydroxy-3-methoxy-(or -3-ethoxy-)benzaldehyde, 2-hydroxy-4-methoxy-(or -4-ethoxy-)benzaldehyde, 2-hydroxy-5-methoxy-(or -5-ethoxy-)benzaldehyde, 2-hydroxy-3-methyl-(or -3-ethyl-)benzaldehyde, 2-hydroxy-5-methyl-(or -5-ethyl-)benzaldehyde, 2-hydroxy-6-methyl-(or -6-ethyl-)benzaldehyde, 2-hydroxy-3-chloro-(or -3-fluoro-)benzaldehyde, 2-hydroxy-5-chloro-(or -5-fluoro-)benzaldehyde, 2-hydroxy-6-chloro-(or -6-fluoro-)benzaldehyde, 2-hydroxy-3-nitro-benzaldehyde, 2-hydroxy-4-nitro-benzaldehyde and 2-hydroxy-5-nitro-benzaldehyde.

The chelate formed by cobalt or manganese with the product resulting from the condensation of ethylenediamine and 2-hydroxy-benzaldehye is particularly suitable.

The chelates employed are known and can be prepared in accordance with the customary processes. The cobalt complexes can be prepared, for example, in accordance with the method of Bailes et al., J. Am. Chem. Soc., 69, 1886 (1947): an aqueous solution of cobalt acetate is mixed with an alcoholic solution of a suitable Schiff's base at a high temperature, optionally in the presence of an alkaline base, and then the crystalline precipitate formed is filtered off, washed with water and then dried in vacuo. The manganese complexes are synthesized in accordance with the same procedure described above.

The amount of chelate used to carry out the reaction, expressed as the number of gram atoms of cobalt or manganese per mol of $\beta$-ethylenically unsaturated ketone, can vary within proportions ranging from $10^{-6}$ to 0.2: it has been found that proportions ranging from $10^{-6}$ to 0.05 are sufficient to carry out the oxidation rapidly.

The oxidation reaction is carried out in the presence of an inorganic or organic base. It is possible to use sodium hydroxide, potassium hydroxide, an alkali metal alcoholate such as sodium or potassium methylate (or ethylate) or a quaternary ammonium hydroxide (trimethylbenzylammonium hydroxide).

Alkylamines and preferably secondary or tertiary amines such as dimethylamine, diethylamine, diisobutylamine, trimethylamine, triethylamine and triisobutylamine may be mentioned as basic agents which are particularly suitable for use in the invention.

The amount of base employed, expressed as the number of mols of base per mol of $\beta$-ethylenically-unsaturated ketone, can vary, without disadvantage, within wide limits, for example, between 0.01 to 10, but it is generally preferable to use amounts between 0.1 and 4.

The process of the invention takes place in an inert organic solvent which is liquid under the conditions of the reaction. It is possible to use aromatic hydrocarbons such as benzene, toluene or xylene; chlorinated aliphatic hydrocarbons such as chloroform or lower aliphatic alcohols such as methanol, ethanol or propanol; saturated or unsaturated aliphatic or cycloaliphatic ketones such as acetone, methyl isobutyl ketone or $\alpha$-isophorone; linear or cyclic carboxamides such as dimethylformamide or N-methylpyrrolidone; and aliphatic or aromatic nitriles such as acetonitrile, propionitrile or benzonitrile; but it is preferred to use solvents of the ether type such as methyl ether, ethyl ether, butyl ether, dimethoxyethane, the dimethyl ether of diethylene glycol, tetrahydrofurane or dioxane.

Moreover, as the reaction solvent, it is possible to use the alkylamine as defined above.

Among all these solvents, it has been found that it is advantageous to use ethyl ether, dimethoxyethane or methyl isobutyl ketone.

In certain cases, the organic phase can contain water and it has even been found that its presence increases the reaction rate.

The concentration of the $\beta$-ethylenically-unsaturated ketone employed in the medium is not critical.

According to the process of the invention, the oxidation advantageously takes place at a temperature of $-30°$ to $+60°$ C., and preferably $-10°$ to $+45°$ C. The reaction can take place either at atmospheric pressure, or at a higher pressure. The oxygen partial pressures can vary within rather wide limits and more particularly from 0.2 to 20 bars; in general, a higher pressure increases the reaction rate.

The process of the invention is valuable because it makes it possible to obtain 3,5,5-trimethyl-cyclohex-2-ene-1, 4-dione by oxidation of $\beta$-isophorone: the practical value of this dione resides in the possibility of aromatizing it to give trimethylhydroquinone, an important starting material used as a precursor of vitamin E.

The reagents and the working conditions of the process which form the subject of the present invention are very particularly suitable for enabling it to be carried out continuously.

SPECIFIC DESCRIPTION OF THE INVENTION

In order to disclose more clearly the nature of the present invention, the following examples illustrating the invention are given. It should be understood, however, that this is done solely by way of example and is intended neither to delineate the scope of the invention nor limit the ambit of the appended claims. In the examples which follow, and throughout the specification, the quantities of material are expressed in terms of parts of weight, unless otherwise specified.

In the examples:
the cobalt chelate derived from the Schiff's base prepared by the condensation of ethylenediamine and 2-hydroxy-benzaldehyde will be denoted by "Co-salen,"
the cobalt chelate derived from the Schiff's base prepared by the condensation of ethylenediamine and 2-hydroxy-3-nitrobenzaldehyde will be denoted by "Co-3-nitro-salen,"
and
the manganese chelate derived from the Schiff's base prepared by the condensation of ethylenediamine and 2-hydroxy-benzaldehyde will be denoted by "Mn-salen".

EXAMPLE 3

A 125 cm.³ glass flask provided with a blade stirrer and connected to a reservoir of pure oxygen at atmospheric pressure and equipped so that it is possible to follow the consumption of gas with the passage of time, is used.

The following compounds are introduced into this reactor: 3.386 g. (2.45 + $10^{-2}$ mol) of $\beta$-isophorone, 0.992 g. (9.8 + $10^{-3}$ mol) of triethylamine, 25 cm.³ of acetonitrile and 0.302 g. (corresponding to 9.3 + $10^{-4}$ gram atom of cobalt) of Co-salen.

The reactor is purged with oxygen and is then placed in communication with the oxygen reservoir. Stirring is started up, while keeping the temperature of the medium at 30° C. during the oxidation reaction.

The reaction is stopped after 50 minutes, the consumption of oxygen having ceased.

The balance of the reaction, that is to say, the yield of 3,5,5-trimethyl-cyclohex-2-ene-1,4-dione relative to the $\beta$-isophorone employed, is determined by vapor phase chromatographic analysis of the reaction mixture.

The degree of conversion of 62-isophorone is found to be 91.4% and the yield of 3,5,5-trimethyl-cyclohex-2-ene-1,4-dione is as much as 62.8% relative to the $\beta$-isophorone employed.

EXAMPLE 2

The following compounds are introduced into the equipment described above in Example 1: 1.981 g. (1.96 + $10^{-2}$ mol) of triethylamine, 23.7 cm.$^3$ of acetonitrile and 0.307 g. (corresponding to 9.6 + $10^{-4}$ gram atom of manganese) of Mn-salen.

The reactor is purged with oxygen and is then placed in communication with the oxygen reservoir.

Stirring is started up and 3.292 g. (2.38 + $10^{-2}$ mol) of β-isophorone are run in slowly over the course of 28 minutes, while keeping the temperature of the reaction medium at 30° C.

When the absorption of oxygen ceases, stirring is stopped and, by vapor phase chromatography, the degree of conversion is found to be 98.9% and the yield of 3,5,5-trimethylcyclohex-2-ene-1,4-dione is found to be 72.2% relative to the β-isophorone employed.

EXAMPLE 3

The following compounds are introduced into the same equipment as described in Example 1: 3.384 g. (2.45 + $10^{-2}$ mol) of β-isophorone, 0.989 g. (9.8 + $10^{-3}$ mol) of triethylamine, 25 cm.$^3$ of dimethoxyethane, 2.4 cm.$^3$ of water and 0.0205 g. (corresponding to 6.4 + $10^{-5}$ gram atom of manganese) of Mn-salen.

The same procedure as above is used but the oxidation is allowed to take place at ambient temperature, namely, 23° C.; slight exothermicity is then observed. The original temperature is re-established by means of a bath of cold water.

After 50 minutes, the reaction is stopped and, by chromatographic analysis, the yield of 3,5,5-trimethyl-cyclohex-2-ene-1,4-dione is found to be 100% relative to the β-isophorone employed.

EXAMPLE 4

The following compounds are introduced into a 2 liter flask equipped with a stirrer and a dropping funnel: 30.368 g. (0.3 mol) of triethylamine, 0.312 g. (corresponding to 9.7 + $10^{-4}$ gram atom of manganese) of Mn-salen, 72 cm.$^3$ of water and 658 cm.$^3$ of dimethoxyethane.

The reaction is carried out at ambient temperature and oxygen is bubbled into the reaction medium at a rate of 75 per hour. 103.67 g. (0.75 mol) of β-isophorone are then run in over the course of 35 minutes: since the reaction is exothermic, the reaction mixture is cooled by means of a bath of cold water. When the addition of β-isophorone is complete, reaction is allowed to take place for a further 1 hour 10 minutes.

The dimethoxyethane, the triethylamine and a part of the water are then evaporated in vacuo (10 mm Hg): a liquid residue of 134.7 g. is obtained; this residue contains the dione which is steam-distilled. A 2 liter aqueous distillate is collected which, when decanted, makes it possible to obtain 65.4 g. of dione and an aqueous phase which is extracted with 7 times 200 cm.$^3$ of ether. The ether phase obtained and the dione previously collected are dried over 100 g. of sodium sulphate. After filtration, the solvent is evaporated to dryness.

97.6 g. of 3,5,5-trimethyl-cyclohex-2-ene-1,4-dione in the form of a yellow-colored liquid are than obtained; the yield relative to the β-isophorone employed is 85.5%.

EXAMPLES 5 to 15

The procedure of Example 1 is followed, but the nature of the chelate and of the solvent, the amounts of each reagent employed, and the temperature are varied.

The conditions and results are listed in the following table.

| EX. | NATURE OF THE CATALYST | NATURE OF THE BASE | NATURE OF THE SOLVENT | AMOUNT OF β-ISOPHORONE INTRODUCED | AMOUNT OF CATALYST INTRODUCED | AMOUNT OF BASE INTRODUCED | AMOUNT OF SOLVENT INTRODUCED | Ratio of chelate to β-isophorone in gram atom of metal/mol | Molar ratio of base to β-isophorone | TEMP. °C | DURATION (in minutes) | Degree of conversion of β-isophorone (%) | Yield of 3,5,5-trimethyl-cyclohex-2-ene-1,4-dione relative to β-isophorone employed (%) |
|---|---|---|---|---|---|---|---|---|---|---|---|---|---|
| 5 | Co-nitro-3-salen | triethyl-amine | aceto-nitrile | 3.275 g (2.37 × 10⁻² mol) | 0.39 g (9.4 × 10⁻² mol) | 0.989 g (9.8 × 10⁻³ mol) | 25 cm³ (10⁻³ mol) | 0.040 | 0.41 | 30 | 35 | 65.8 | 51.1 |
| 6 | Mn salen | " | " | 3.389 g (2.45 × 10⁻² mol) | 0.3015 g (9.4 × 10⁻⁴ mol) | 0.983 g (9.7 × 10⁻³ mol) | 25 cm³ | 0.038 | 0.40 | −2 | 105 | 98.5 | 74.4 |
| 7 | " | " | " | 3.381 g (2.45 × 10⁻² mol) | 0.300 g (9.3 × 10⁻⁴ mol) | 0.985 g (9.7 × 10⁻³ mol) | 25 cm³ | 0.038 | 0.40 | −15 | 220 | 89.6 | 66.6 |
| 8 | " | " | chloro-form | 3.400 g (2.46 × 10⁻² mol) | 0.2999 g (9.3 × 10⁻⁴ mol) | 0.980 g (9.7 × 10⁻³ mol) | 25 cm³ | 0.038 | 0.39 | −2 | 300 | 84.1 | 68.5 |
| 9 | " | " | ethyl ether | 3.393 g (2.45 × 10⁻² mol) | 0.3025 g (9.4 × 10⁻⁴ mol) | 0.984 g (9.7 × 10⁻³ mol) | 25 cm³ | 0.038 | 0.40 | 23 | 320 | 97 | 88.6 |
| 10 | " | " | dimethoxy-ethane | 3.388 g (2.45 × 10⁻² mol) | 0.060 g (1.9 × 10⁻⁴ mol) | 0.983 g (9.8 × 10⁻³ mol) | 25 cm³ | 0.008 | 0.40 | 23 | 240 | 97.5 | 97.1 |
| 11 | " | " | dimethoxy-ethane and water | 3.381 g (2.45 × 10⁻² mol) | 0.0054 g (1.7 × 10⁻⁵ mol) | 0.988 g (9.8 × 10⁻³ mol) | 25 cm³ 2.4 cm³ | 0.0007 | 0.40 | 23 | 80 | 100 | 100 |
| 12 | " | " | triethyl-amine | 3.256 g (2.36 × 10⁻² mol) | 0.3010 g (9.4 × 10⁻⁴ mol) | 19.211 g (1.9 × 10⁻¹ mol) | 26.3 cm³ | 0.040 | 8.05 | −2 | 275 | 100 | 72.7 |
| 13 | " | " | aceto-nitrile | 3.386 g (2.45 × 10⁻² mol) | 0.3015 g (9.4 × 10⁻⁴ mol) | 0.490 g (4.8 × 10⁻³ mol) | 25.7 cm³ | 0.038 | 0.20 | −2 | 180 | 100 | 76.7 |
| 14 | " | " | α-iso-phorone | 3.39 g (2.45 × 10⁻² mol) | 0.010 g (3.1 × 10⁻⁵ mol) | 0.98 g (9.7 × 10⁻³ mol) | 25 cm³ | 0.0013 | 0.40 | 23 | 205 | 88.9 | 77.6 |
| 15 | " | " | methyl isobutyl ketone | 3.39 g (2.45 × 10⁻² mol) | 0.010 g (3.1 × 10⁻⁵ mol) | 0.98 g (9.7 × 10⁻³ mol) | 25 cm³ | 0.0013 | 0.40 | 23 | 100 | 97.6 | 85.8 |

In each of the foregoing examples, the β-isophorone may be replaced by an equivalent amount of pent-4-en-2-one, 4-methyl-pent-4-en-2-one, hex-5-en-3-one, 3,4-dimethyl-hex-4-en-2-one, 4-methyl-3-ethyl-hex-4-en-2-one, hept-1-en-4-one, 6-methyl-hept-4-en-2-one, 2-methyl-hept-5-en-3-one, cyclopent-3-en-1-one, cyclohex-3-en-1-one, 5,5-dimethyl-cyclohex-3-en-1-one, 2,5,5-trimethyl-cyclohex-3-en-1-one, 2,5,6-trimethyl-cyclohex-3-en-1-one, 2,6,6-trimethyl-cyclohex-3-en-1-one, 2,5,6,6-tetramethyl-cyclohex-3-en-1-one, 5,5-dimethyl-2-ethyl-cyclohex-3-en-1-one, 2-methyl-5-isopropyl-cyclohex-3-en-1-one, 5,5-dimethyl-2-isopropyl-cyclohex-3-en-1-one, and cyclooct-3-en-1-one.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed.

What we claim is:

1. A process for the preparation of 3,5,5-trimethylcyclohex-2-ene-1,4-dione by oxidation of β-isophorone, which comprises oxidizing the β-isophorone with molecular oxygen or a gas containing molecular oxygen, in a liquid organic solvent medium in the presence of an alkylamine and a chelate of the general formula:

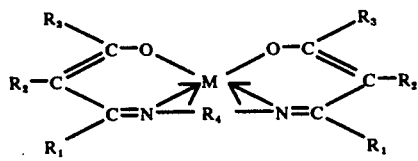

(I)

in which:

M represents cobalt or manganese, $R_1$, $R_2$ and $R_3$, which may be identical or different, each represents a hydrogen atom or an alkyl radical containing 1 to 4 carbon atoms; or $R_2$ and $R_3$, together with the 2 carbon atoms of the double bond, form a benzene ring carrying one or more hydrogen or halogen atoms, nitro groups, alkyl radicals containing 1 to 4 carbon atoms or alkoxy radicals containing 1 to 4 carbon atoms, and $R_4$ represents a divalent hydrocarbon radical containing 2 to 15 carbon atoms or an alkyl chain interrupted by one or more heteroatoms and containing from 4 to 10 carbon atoms.

2. A process according to claim 1, wherein the chelate is one in which $R_2$ and $R_3$, together with the 2 carbon atoms of the double bond, form a benzene ring optionally substituted by a nitro group.

3. A process according to claim 1, wherein the chelate is one in which $R_1$ is a hydrogen atom.

4. A process according to claim 1, wherein the chelate is one in which $R_4$ is an ethylene or propylene radical.

5. A process according to claim 1, wherein the heteroatom in $R_4$ is oxygen or nitrogen.

6. A process according to claim 1, wherein the chelate is a condensation product of ethylenediamine and 2-hydroxybenzaldehyde, or of ethylenediamine and 2-hydroxy-3-nitrobenzaldehyde.

7. A process according to claim 1, wherein the chelate is present in an amount to provide $10^{-6}$ to 0.2 gram atom of cobalt or manganese per mol of β-ethylenically unsaturated ketone.

8. A process according to claim 7, wherein the amount of $10^{-5}$ to 0.05 gram atoms.

9. A process according to claim 1, wherein the alkylamine is a member selected from the class of secondary and tertiary alkyl amines.

10. A process according to claim 9, wherein the base is a member selected from the class consisting of dimethylamine, diethylamine, diisobutylamine, trimethylamine, triethylamine and triisobutylamine.

11. A process according to claim 1, wherein the molar ratio of alkylamine to β-isophorone is 0.01:1 to 10:1.

12. A process according to claim 11, wherein the ratio is 0.1:1 to 4:1.

13. A process according to claim 1, wherein the reaction solvent is a member selected from the class consisting of an aromatic hydrocarbon, chlorinated aliphatic hydrocarbon, lower aliphatic alcohol, saturated and unsaturated aliphatic and cycloaliphatic ketones, linear and cyclic carboxamides, aliphatic and aromatic nitriles, secondary and tertiary amines and an ether.

14. A process according to claim 13, wherein the reaction solvent is a member selected from the class consisting of acetonitrile, chloroform, ethyl ether, dimethoxyethane, triethylamine, a mixture of dimethoxyethane and water, α-isophorone and methyl isobutyl ketone.

15. A process according to claim 1, wherein the oxidation is carried out at a temperature of −30° to +60° C., at atmospheric pressure or under pressure.

16. A process according to claim 15, wherein the temperature is −10° to +45° C.

* * * * *

UNITED STATES PATENT AND TRADEMARK OFFICE
CERTIFICATE OF CORRECTION

PATENT NO. : 4,026,947
DATED : May 31, 1977
INVENTOR(S) : Michel Costantini et al.

It is certified that error appears in the above-identified patent and that said Letters Patent are hereby corrected as shown below:

Col. 4, line 42, "EXAMPLE 3" should read -- EXAMPLE 1 --.

Col. 4, line 65, "62-isophorone" should read -- β-isophorone --.

Col. 5, line 25, "(2.45 + $10^{-2}$ mol)" should read:
    -- (2.45 x $10^{-2}$ mol) --.

Col. 5, line 25, "(9.8 + $10^{-3}$ mol)" should read:
    -- (9.8 x $10^{-3}$ mol) --.

Col. 5, line 28, "(6.4 + $10^{-5}$ mol)" should read:
    -- (6.4 x $10^{-5}$ mol) --.

Col. 6, line 6, "9.7 + $10^{-4}$" should read -- 9.7 x $10^{-4}$ --.

Table at Col. 7 of patent:

Col. 5 of table, entry corresponding to Example 5:

"3.275 g    "     should read:     -- 3.275 g    --
    (2.37 x                    (2.37 x $10^{-2}$ mol)

UNITED STATES PATENT AND TRADEMARK OFFICE
CERTIFICATE OF CORRECTION

PATENT NO. : 4,026,947
DATED : May 31, 1977
INVENTOR(S) : Michel Costantini et al.

It is certified that error appears in the above-identified patent and that said Letters Patent are hereby corrected as shown below:

Col. 6 of table, entry corresponding to Example 5:

"0.39 g ($9.4 \times 10^{-2}$ mol)" should read: -- 0.39 g ($9.4 \times 10^{-4}$ mol) --

Col. 7 of table, entry corresponding to Example 5:

"0.989 g ($9.9 \times 10^{-4}$ mol)" should read: -- 0.989 g ($9.8 \times 10^{-3}$ mol) --

Col. 7 of table, entry corresponding to Example 10:

"0.983 g ($9.8 \times 10^{-3}$ mol)" should read: -- 0.988 g ($9.8 \times 10^{-3}$ mol) --

UNITED STATES PATENT OFFICE
CERTIFICATE OF CORRECTION

Patent No. 4,026,947                Dated May 31, 1977

Inventor(s) Michel Costantini et al.

It is certified that error appears in the above-identified patent and that said Letters Patent are hereby corrected as shown below:

Column 8 of table, entry corresponding to Example 6:

"$10^{-3}$ mol)"        should read        -- 25 cm$^3$ --.
25 cm$^3$

Signed and Sealed this

Sixth Day of September 1977

[SEAL]

Attest:

RUTH C. MASON                LUTRELLE F. PARKER
*Attesting Officer*          *Acting Commissioner of Patents and Trademarks*